US010478066B2

(12) United States Patent
Reinhardt et al.

(10) Patent No.: US 10,478,066 B2
(45) Date of Patent: Nov. 19, 2019

(54) SYSTEM AND METHOD FOR DETECTION OF CRAVINGS IN INDIVIDUALS WITH ADDICTION

(71) Applicants: Megan Reinhardt, Bristol, MA (US); Nicole Gilbertson, Huntington Beach, CA (US)

(72) Inventors: Megan Reinhardt, Bristol, MA (US); Nicole Gilbertson, Huntington Beach, CA (US)

(*) Notice: Subject to any disclaimer, the term of this patent is extended or adjusted under 35 U.S.C. 154(b) by 172 days.

(21) Appl. No.: 15/681,111

(22) Filed: Aug. 18, 2017

(65) Prior Publication Data

US 2018/0014729 A1    Jan. 18, 2018

(51) Int. Cl.
*A61B 5/00* (2006.01)
*A61B 5/11* (2006.01)

(52) U.S. Cl.
CPC .......... *A61B 5/0008* (2013.01); *A61B 5/1118* (2013.01); *A61B 5/4848* (2013.01); *A61B 5/4884* (2013.01); *A61B 5/6801* (2013.01); *A61B 5/6843* (2013.01)

(58) Field of Classification Search
CPC ... A61B 5/0008; A61B 5/1118; A61B 5/4848; A61B 5/4884; A61B 5/6801; A61B 5/6843
USPC .......................................................... 607/58
See application file for complete search history.

(56) References Cited

U.S. PATENT DOCUMENTS

| | | | | |
|---|---|---|---|---|
| 9,782,122 | B1* | 10/2017 | Pulliam | A61B 5/4824 |
| 2005/0039742 | A1* | 2/2005 | Hickle | A61M 16/026 |
| | | | | 128/203.14 |
| 2008/0208016 | A1* | 8/2008 | Hughes | A61B 5/0533 |
| | | | | 600/301 |
| 2010/0268056 | A1* | 10/2010 | Picard | A61B 5/0531 |
| | | | | 600/388 |
| 2011/0004072 | A1* | 1/2011 | Fletcher | A61B 5/0002 |
| | | | | 600/300 |
| 2012/0296175 | A1* | 11/2012 | Poh | A61B 5/02405 |
| | | | | 600/301 |
| 2013/0079602 | A1* | 3/2013 | Picard | A61B 5/0022 |
| | | | | 600/301 |
| 2013/0080185 | A1* | 3/2013 | Picard | A61B 5/0022 |
| | | | | 705/2 |
| 2014/0316229 | A1 | 10/2014 | Tognetti et al. | |
| 2015/0148621 | A1* | 5/2015 | Sier | A61B 5/7267 |
| | | | | 600/301 |
| 2017/0112407 | A1* | 4/2017 | Wu | G16H 50/30 |
| 2017/0347906 | A1* | 12/2017 | Intrator | A61B 5/0478 |

(Continued)

*Primary Examiner* — Christopher A Flory
(74) *Attorney, Agent, or Firm* — Kenneth L. Green; Averill & Green

(57) ABSTRACT

A system and method detects and provides alerts when a subject's physiological measurements indicate a likelihood of the presence of drug cravings and a possible return to drug use. The system includes a wearable sensor which monitors movement in three dimensions, Electro Dermal Response (EDR), and temperature. Initially, training measurements are taken while subject is under supervision and not taking drugs, and algorithms process the measurements to determine thresholds. After release from supervision, the physiological measurements are monitored, processed, and compared to the thresholds. When the comparison indicates a presence of cravings for drugs, an alert is provided to the subject and/or to monitoring personnel.

19 Claims, 3 Drawing Sheets

(56) References Cited

U.S. PATENT DOCUMENTS

| | | | |
|---|---|---|---|
| 2018/0001184 A1* | 1/2018 | Tran | H04N 5/2257 |
| 2018/0068080 A1* | 3/2018 | Parate | G06F 19/3418 |
| 2018/0228695 A1* | 8/2018 | Valentine | G06F 19/30 |
| 2018/0308569 A1* | 10/2018 | Luellen | G16H 20/10 |

\* cited by examiner

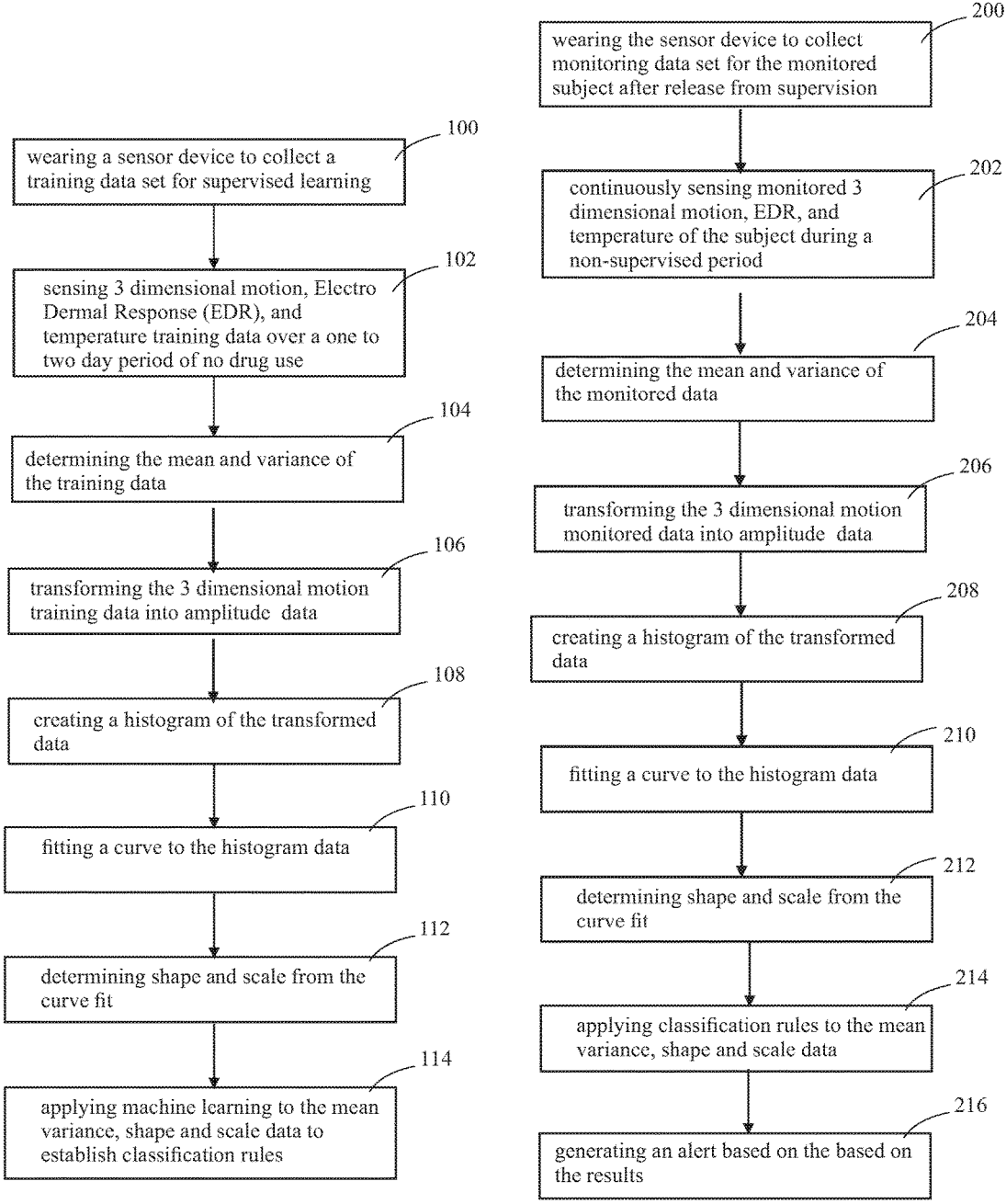

SYSTEM AND METHOD FOR DETECTION OF CRAVINGS IN INDIVIDUALS WITH ADDICTION

BACKGROUND OF THE INVENTION

The present invention relates to addressing drug addiction and in particular to monitoring the level of cravings of an addict attempting to overcome their addiction.

Drug addiction is an increasingly serious individual and societal issue. The rate of drug addiction in the United States has reached levels where this addiction affects not only the addict, but society as a whole. Many addicts recognize their personal damage due to the use of drugs and desire to overcome their addiction through various programs. The individuals often successfully complete a program, but are not able to remain drug free after re-entering society, especially when they are subject to the stress that both existed in the past, and stress produced by social issues they encounter when they attempt to rejoin society. Such stress often results in cravings to resume drug use. A need exists for identifying the presence of stress and the resulting cravings to allow intervention before a return to drug use.

BRIEF SUMMARY OF THE INVENTION

The present invention addresses the above and other needs by providing a system and method which detects and provides alerts when a subject's physiological measurements indicate a likelihood of the presence of drug cravings and a possible to return to drug use. The system includes a wearable sensor which monitors movement in three dimensions, Electro Dermal Response (EDR), and temperature. Initially, training measurements are taken while subject is under supervision and not taking drugs, and algorithms process the measurements to determine thresholds. After release from supervision, the physiological measurements are monitored, processed, and compared to the thresholds. When the comparison indicates a presence of cravings for drugs, an alert is provided to the subject and/or to monitoring personnel.

In accordance with another aspect of the invention, there is provided a system to detect an individual subject's stress, cravings, and use of drugs, based on physiological sensors, advanced signal processing and a machine learning framework. A wearable sensor suit is worn by a subject recovering from drug use. The sensor suit produces signals by measuring physiological parameters such as three dimensions of body movement (locomotor activity), EDR and temperature. Statistical data (e.g., the mean and variance) of the three dimensional movement, EDR, and temperature parameters are computed. The statistical features may be used to assess cravings and/or stress in the individual subject. The physiological data is processed in windows having a length L, for example, five minute window.

In accordance with still another aspect of the invention, there is provided a system to determine shape and scale parameters of a distribution of amplitudes of the three dimensional movement data are computed. Amplitudes, frequencies, and phases of the three dimensions of motion signals may be obtained using an appropriate transform. The distribution of amplitudes provides a sensitive measure capable of detecting the frequency of use of drugs (heavy use vs. moderate use). Dynamic features such as instantaneous fluctuations of amplitudes, frequencies, and phases at multiple time scales may be obtained by the time-frequency decomposition of these signals using an appropriate transform, for example the Hilbert or a wavelet transform approach In accordance with yet another aspect of the invention, there is provided a method for adapting a drug use risk detection method to an individual subject prior to release from a treatment facility. A training data set comprising statistical and dynamic features is collected and incorporated in a machine learning framework. The data is collected over a one to two day period where the individual is monitored to ensure that there is no drug use. The processed three dimensional motion signals, the EDR, and temperature signals, are processed by machine learning algorithms to establish boundaries for non-drug use. The machine learning framework is tailored specifically to individual subjects to assess pathological fluctuations in the physiological signals that can be used later assess the risk or return to drug use.

In accordance with another aspect of the invention, there is provided a method for dejection of cravings. Following release of the individual subject from a treatment facility, the individual subject is provided with a wearable device measuring physiological data. The wearable device continuously measures physiological signals, and the signals are processed for relevant features related to cravings. An alert is provided to the individual subject and/or a provider through of any imminent risk of using illicit drugs or cravings. By accurately tracking the statistical and dynamic fluctuations in these physiological signals in real time, the method can provide accurate detection of cravings.

In accordance with yet another aspect of the invention, there is provided a method for providing alerts to a care giver. The present system includes non-invasive wearable biosensors that stream data continuously in real time to a processor which processes the physiological signals and executes a craving or risk detection software. Once a specific threshold of risk has reached, the algorithm can trigger an alert through a smart phone to a user or a care giver or a provider.

In accordance with still another aspect of the invention, there is provided a method for providing alerts based on a 16 dimension vector space of ten physiological signals comprising mean and variance of three dimensional motion, EDR, and temperature, and six spatial features comprising shape and scale of histogram data.

In accordance with another aspect of the invention, there is provided a wearable sensor monitoring three dimensional data at a 32 samples per second, EDR data at four samples per second, and temperature data at one sample per second. The data is provided in windows of about 5 minute length.

In accordance with still another aspect of the invention, there is provided a monitoring system including a wearable sensor, a smart phone type device, and a monitoring facility. Data collected by the wearable sensor may be processed in the wearable sensor, in the smart phone type device, or at the monitoring facility. In some embodiments, the wearable sensor and smart phone type device may be a single device.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 3 shows a method for processing the individual physiological parameters measured during an unsupervised period to detect stress, cravings, and drug use.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Where the terms "about" or "generally" are associated with an element of the invention, it is intended to describe a feature's appearance to the human eye or human perception, and not a precise measurement.

Figure 1:
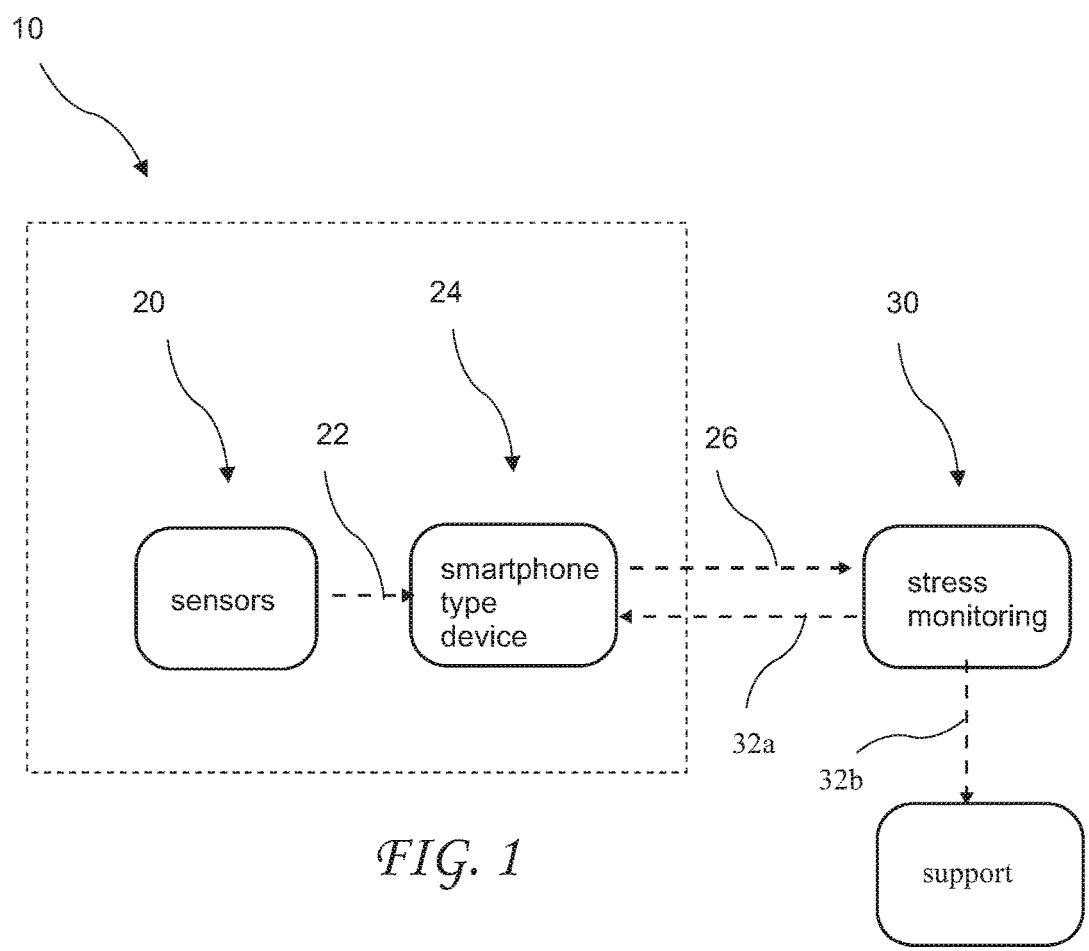
FIG. 1 shows components of a system for sensing physiological parameters and detecting cravings based on the FIG. 2 shows a method for processing the individual physiological parameters to detected cravings according to the present invention.

Components of a system for detection of cravings in individuals with addiction according to the present invention are shown in FIG. 1. The system includes wearable devices 10 comprising sensor suit 20 and a smart phone type device 24 carried by the individual. The sensor suit 20 measures physiological parameters including three dimensional body movement, Electro Dermal Response (EDR), and temperature. A suitable sensor suit is described in US Patent Application Publication No. 2014/0316229 for "Apparatus for Electrodermal Activity Measurement with Current Compensation" filed 17 Mar. 2014. The sensor suit 20 includes at least one accelerometer, a temperature sensor, and EDR sensor. The '229 publication is incorporated by reference in its entirety into the present specification.

The sensor suit 20 preferably wirelessly communicates with a smart phone type device 24 to provide data 22 to the smart phone type device 24. The wireless communication may be, for example, Bluetooth communication. While Bluetooth is a preferred wireless interface, those skilled in the art will recognize other types of communication, including wired, and a system according to the present including any form of communication between the sensors and the smart phone type device, and the sensor suit 20 and smart phone type device 24 may be a single device.

The smart phone type device 24 receives the three dimensional movement, the EDR, and temperature signals 22 from the sensor suit 20 and transits the data 26 to a stress monitoring center 30. If the cravings exceed a threshold, or advanced processing indicates a craving, the stress monitoring center 30 may provide alerts 32a back to the subject and alerts 32b to support personnel. The data may be processed in the sensor suit 20, the smart phone type device 24, or at the stress monitoring center 30, and the processing may be distributed over the sensor suit 20, the smart phone type device 24, and the stress monitoring center 30. Those skilled in the art will recognize that any distribution of the method between devices is intended to come within the scope of the present invention.

A method for processing the individual physiological parameters measured during a period of supervised no drug use to establish classification rules is shown in FIG. 2. The method includes wearing a sensor device to collect a training data set for supervised learning at step 100, sensing 3 dimensional motion, Electro Dermal Response (EDR), and temperature training data over a one to two day period of supervised no drug use by the wearer at step 102, determining the mean and variance of the training data at step 104, transforming the 3 dimensional motion training data into amplitude data at step 106, creating a histogram of the transformed data at step 108, fitting a curve to the histogram data at step 110, determining shape and scale from the curve fit at step 112, applying machine learning to the mean variance, shape and scale data to establish classification rules at step 114. Examples of transforms used in steps 106 and 206 are a Hilbert transform or a wavelet transform. Examples of curves applied to the curve fit of steps 110 and 210 are fitting a gamma function to the amplitude data.

A method for processing the individual physiological parameters measured during an unsupervised period to detect stress, cravings, and drug use, is shown in FIG. 3. The method includes wearing the sensor device to collect monitoring data set for the monitored subject after release from supervision at step 200, continuously sensing monitored three dimensional motion, EDR, and temperature of the subject during a non-supervised period is shown in step 202, determining the mean and variance of the monitored data is shown in step 204, transforming the three dimensional motion monitored data into amplitude data is shown in step 206, creating a histogram of the transformed data is shown in step 208, fitting a curve to the histogram data is shown in step 210, determining shape and scale from the curve fit is shown in step 212, applying classification rules to the mean variance, shape and scale data is shown in step 214, and generating an alert based on the results is shown in step 216. The alerts may be provided to the subject and/or to a monitor and may be an alert for stress, for cravings, or of drug use.

Figure 4:
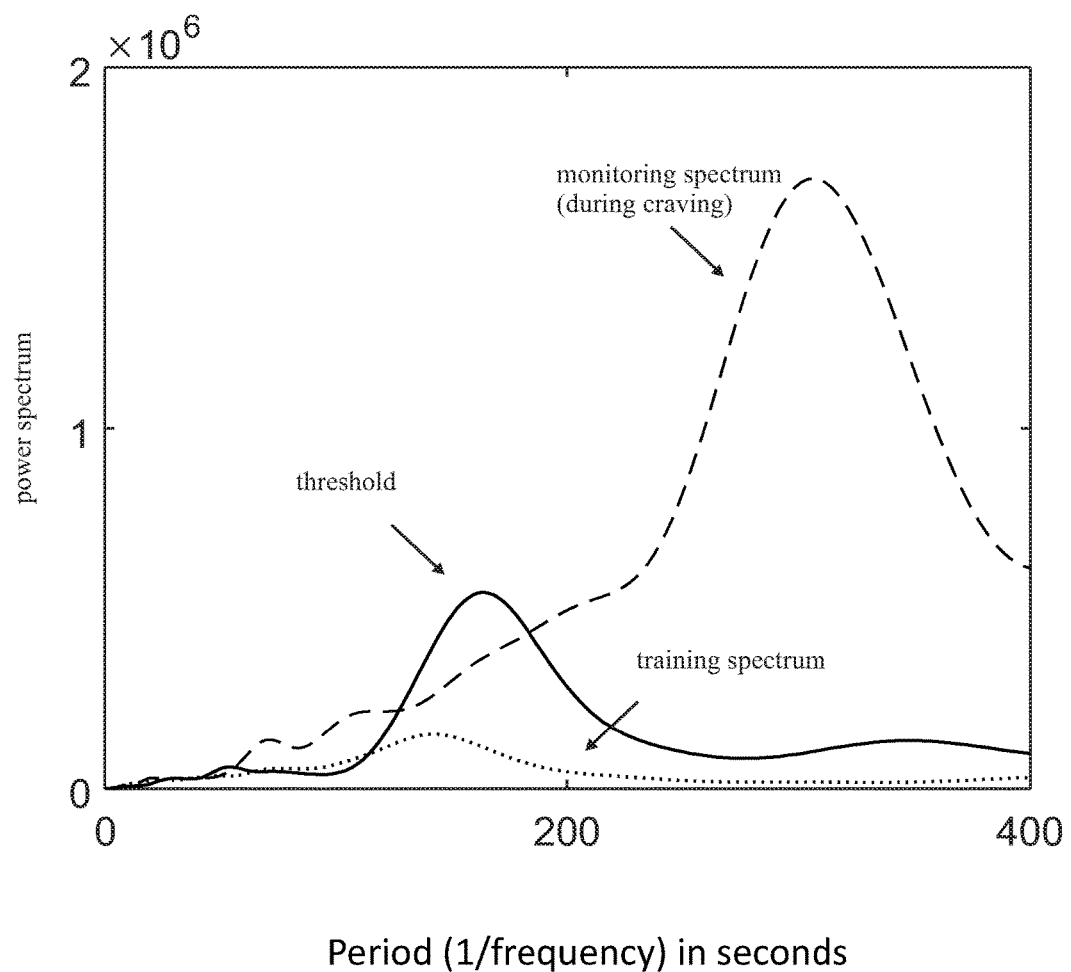
FIG. 4 shows a plot of a training spectrum, a monitoring spectrum, and a threshold.

A plot of a training spectrum, a monitoring spectrum, and a threshold are shown in FIG. 4.

While the invention herein disclosed has been described by means of specific embodiments and applications thereof, numerous modifications and variations could be made thereto by those skilled in the art without departing from the scope of the invention set forth in the claims.

We claim:

1. A method for detecting drug craving of an individual subject, comprising:

the individual subject undergoing a period of supervision wearing physiological sensors, the physiological sensors configured to measure training motion of the individual subject in at least one dimension;

producing training motion data in the at least one dimension by sensing the training motion of the subject during a period of no drug use;

generating training statistics of the training motion data during the period of no drug use;

determining classification rules for the training statistics during the period of no drug use;

releasing the individual subject from the period of supervision;

producing monitoring motion data in the at least one dimension by sensing monitoring motion of the subject during a period of non-supervision;

generating monitoring statistics of the monitoring motion data during the period of non-supervision;

comparing the monitoring statistics during the period of non-supervision to the classification rules; and providing a warning of drug cravings when the monitoring statistics exceed the thresholds.

2. The method of claim 1, wherein:
sensing the training motion comprises sensing training accelerometer data; and
sensing monitoring motion comprises sensing monitoring accelerometer data.

3. The method of claim 2, wherein:
generating training statistics comprises computing training mean and training variance of the training accelerometer data and determining the classification rules of the training statistics comprises determining classification rules of the mean and the variance of the training mean and the training variance; and
generating monitoring statistics comprises computing monitoring mean and monitoring variance of the monitoring accelerometer data and comparing the monitoring statistics comprises comparing the monitoring mean and the monitoring variance to the classification rules.

4. The method of claim 3, further including:
collecting training Electrodermal Response (EDR) and training temperature data during the period of no drug use;
determining a training EDR mean and variance and a training temperature mean and variance;
including the training EDR mean and variance and the training temperature mean and variance in determining the classification rules;
collecting monitoring EDR and monitoring temperature data during the period of non-supervision;
determining monitoring EDR and monitoring temperature mean and variance from the monitoring EDR and the monitoring temperature data; and
including comparing the monitoring EDR mean and variance and monitoring temperature mean and variance to the classification rules to determine if the drug cravings are present.

5. The method of claim 4, wherein the training data and the monitoring data is collected and processed in windows having a length between three and seven minutes.

6. The method of claim 5, wherein the training data and the monitoring data is collected and processed in windows having a length of about five minutes.

7. The method of claim 4, wherein the at least one dimension comprises at least two dimensions.

8. The method of claim 7, wherein the at least one dimension comprises three dimensions.

9. The method of claim 3, wherein the at least one dimension comprises at least two dimensions, and further including:
determining the training mean and variance of the training motion data in the at least two dimensions;
transforming the training motion data into training amplitude data;
creating training histogram data from the training amplitude data;
fitting a training curve to the training amplitude data;
determining training shape and scale based on the training curve;
determining monitoring mean and variance of the monitoring motion data in the at least two dimensions;
transforming the monitoring motion data into monitoring amplitude data;
creating monitoring histogram data from the monitoring amplitude data;
fitting a monitoring curve to the monitoring amplitude data;
determining monitoring shape and scale based on the monitoring curve; and
including comparing the monitoring shape and scale parameters to the shape and scale classification rules to determine if the drug cravings are present.

10. The method of claim 9, wherein;
transforming the training motion data into training amplitude data comprises transforming the training motion data into training amplitude data using a Hilbert transform; and
transforming the monitoring motion data into monitoring amplitude data comprises transforming the monitoring motion data into monitoring amplitude data using a Hilbert transform.

11. The method of claim 9, wherein;
transforming the training motion data into training amplitude data comprises transforming the training motion data into training amplitude data using a wavelet transform; and
transforming the monitoring motion data into monitoring amplitude data comprises transforming the monitoring motion data into monitoring amplitude data using a wavelet transform.

12. The method of claim 9, wherein:
fitting a training curve to the training amplitude data comprises fitting a gamma function to the training amplitude data; and
fitting a monitoring curve to the monitoring amplitude data comprises fitting a gamma function to the training amplitude data.

13. The method of claim 3, wherein the at least one dimension comprises at least two dimensions, and further including:
determining training phase correlation between the at least two dimensions;
determining training classification rules further based on the training phase correlation;
determining monitoring phase correlation between the at least two dimensions;
including comparing the monitoring phase correlation to the classification rules to determine if the drug cravings are present.

14. The method of claim 13, wherein the at least two dimensions are three dimensions.

15. The method of claim 13, wherein the training motion data has a 32 samples per second data rate.

16. The method of claim 1, wherein the training motion data has a 32 samples per second data rate.

17. The method of claim 1, wherein producing training motion data in the at least one dimension comprises producing training motion data in 3 dimensions.

18. A method for detecting drug craving of an individual subject, comprising:
the individual subject undergoing a period of supervision wearing physiological sensors, the physiological sensors configured to measure training motion of the individual subject in three dimensions, training Electrodermal Response (EDR), and training temperature;
recording windows of training motion data in the three dimension, training EDR data, and training temperature data by sensing the training motion, the training EDR, and the training temperature of the subject during a period of no drug use;

generating training mean and variance of: the windows of the training motion data; training EDR data; and training temperature data, during the period of no drug use;

applying machine learning to determining classification rules during the period of no drug use;

releasing the individual subject from the period of supervision to a period of monitoring;

recording: monitoring motion data in the three dimensions; monitoring EDR data; and monitoring temperature data, during the period of monitoring;

generating monitoring mean and variance of: the monitoring motion data; monitoring EDR data; and monitoring temperature data, during the period of monitoring;

comparing the monitoring mean and variance during the period of monitoring to the classification rules; and providing a warning of a condition selected from the group consisting of stress and drug cravings when the comparison indicates the presence of the condition.

19. A method for detecting drug craving of an individual subject, comprising:

the individual subject undergoing a period of supervision wearing physiological sensors, the physiological sensors configured to measure training motion of the individual subject in three dimensions, training Electrodermal Response (EDR), and training temperature;

recording training windows of training motion data in the three dimension, training EDR data, and training temperature data by sensing the training motion, the training EDR, and the training temperature of the individual subject during a period of no drug use;

generating training mean and variance of the training windows of the training motion data, training EDR data, and training temperature data during the period of no drug use;

transforming the three dimensional training motion data in the training windows into training amplitude data;

creating training histogram data of the training amplitude data;

fitting a training curve to the training histogram data;

determining training shape and scale from the training curve;

applying a machine learning to the training mean and variance and training shape and scale determining classification rules during the period of no drug use;

recording monitoring windows of monitoring motion data in the three dimension, monitoring EDR data, and monitoring temperature data by sensing the monitoring motion, the monitoring EDR, and the monitoring temperature of the individual subject during a period of no drug use;

generating monitoring mean and variance of the monitoring windows of the monitoring motion data, monitoring EDR data, and monitoring temperature data during the period of no drug use;

transforming the three dimensional monitoring motion data in the monitoring windows into monitoring amplitude data;

creating monitoring histogram data of the monitoring amplitude data;

fitting a monitoring curve to the monitoring histogram data;

determining monitoring shape and scale from the monitoring curve;

comparing the monitoring mean and variance and monitored shape and scale during the period of monitoring to the classification rules; and providing a warning of a condition selected from the group consisting of stress, drug cravings, and drug use when the comparison indicates the presence of the condition.

* * * * *